United States Patent [19]
Ohno et al.

[11] Patent Number: 5,811,163
[45] Date of Patent: Sep. 22, 1998

[54] IN-MOLD LABEL AND CONTAINER DECORATED THEREWITH

[75] Inventors: Akihiko Ohno; Takatoshi Nishizawa; Masaki Shiina, all of Ibaraki; Junichi Yasuda, Tokyo; Hajime Ikeno; Keiko Shichijo, both of Mie, all of Japan

[73] Assignee: Oji-Yuka Synthetic Paper Co., Ltd., Tokyo, Japan

[21] Appl. No.: 698,053

[22] Filed: Aug. 13, 1996

[30] Foreign Application Priority Data

Feb. 2, 1996 [JP] Japan ................................ 8-039128

[51] Int. Cl.$^6$ .................................................. B32B 27/32
[52] U.S. Cl. ................... 428/35.7; 428/36.5; 428/312.2; 428/516; 428/910; 526/348.1; 215/230
[58] Field of Search .................. 428/35.7, 36.5, 428/513, 516, 910, 312.2; 526/348.1; 215/230; 283/81

[56] References Cited

FOREIGN PATENT DOCUMENTS

| | | |
|---|---|---|
| 436044 | 7/1991 | European Pat. Off. . |
| A0436044 | 7/1991 | European Pat. Off. . |
| A0521479 | 7/1992 | European Pat. Off. . |
| WO9312151 | 6/1993 | WIPO . |

OTHER PUBLICATIONS

Nakano et al, Development of Automatic Cross Fractionation: Combination of Crystallizability.

Fractionation and Molecular Weight Fractionation, 1981, pp. 4217–4231.

*Primary Examiner*—Fred M. Teskin
*Attorney, Agent, or Firm*—Sughrue, Mion, Zinn, Macpeak & Seas, PLLC

[57] ABSTRACT

An in-mold label which has a thermoplastic resin film base layer (I) having printed matter on its front side and, formed on the back side of the thermoplastic resin base layer (I), a heat sealable resin layer (II) having a lower melting point than the constituent resin of the thermoplastic resin film base layer (I), the constituent resin of the heat sealable resin layer (II) having as its main component an ethylene/α-olefin copolymer obtained by copolymerizing from 40 to 98 wt % ethylene and from 60 to 2 wt % of an α-olefin having from 3 to 30 carbon atoms using a metallocene catalyst.

4 Claims, 7 Drawing Sheets

IN-MOLD LABEL AND CONTAINER DECORATED THEREWITH

FIELD OF THE INVENTION

The present invention relates to a label for use in in-mold molding in which the label is initially set in a mold so that the side of the label which is in contact with the mold wall surface contains printed matter, and a parison of a molten thermoplastic resin is introduced into the mold and molded by blow molding or a molten thermoplastic resin sheet is molded in the mold by vacuum forming or air pressure forming to produce a labeled container.

BACKGROUND OF THE INVENTION

A conventional integral molding process for producing a labeled resin container comprises initially inserting a blank or a label in a mold and then molding a container by injection molding, blow molding, differential pressure forming, foam molding, etc., to decorate the container within the mold [see JP-A-58-69015 (the term "JP-A" as used herein means an "unexamined published Japanese patent application") JP-A-59-198149 and EP-A-254923]. Such known in-mold labels include gravure printed resin films, multicolor offset printed synthetic papers [see, for example, JP-B-2-7814 (the term "JP-B" as used herein means an "examined Japanese patent publication") and JP-A-2-84319], and gravure printed aluminum labels comprising an aluminum foil laminated on the back side thereof with high pressure low density polyethylene and an ethylene/vinyl acetate copolymer.

However, the process for producing containers decorated with the aforementioned in-mold labels or blanks through in-mold molding has the following drawbacks. Labels employing a high pressure low density polyethylene as a heat sealable resin show insufficient adhesion to polypropylene containers and peel off the containers, although they show satisfactory adhesion to containers made of high density polyethylene. On the other hand, use of an ethylene/vinyl acetate copolymer as a heat sealable resin results in an increased percentage of label rejects upon label punching because the label sheet containing such a heat sealable resin layer has poor punchability and yields labels having burrs, although the labels employing such a heat sealable resin show improved adhesion to polypropylene hollow containers.

Further drawbacks of the earlier described prior art labels are that the label sheet (a sheet of the label material which can be punched or cut to yield a plurality of labels) has poor suitability for feeding and removal in printing (offset, flexographic, UV offset or letterpress printing) in a label production process, and the labels obtained through cutting or punching suffer blocking at their cut edges or are apt to suffer blocking when piled up.

SUMMARY OF THE INVENTION

An object of the present invention is to provide an in-mold label which shows satisfactory adhesion to a container made of either high density polyethylene or polypropylene, can be easily punched out of a label sheet without forming burrs, and can be easily fed into a mold.

The present invention provides an in-mold label comprising a thermoplastic resin film base layer (I) (hereinafter often simply base layer (I)") carrying printed matter on its front side and, formed on the back side of the base layer (I), a heat sealable resin layer (II) having a lower melting point than the constituent resin of the resin film base layer (I), the constituent resin of the heat sealable resin layer (II) comprising as the main component an ethylene/α-olefin copolymer obtained by copolymerizing from 40 to 98 wt % ethylene and from 60 to 2 wt % of an α-olefin (so as to total 100 wt %) having from 3 to 30 carbon atoms using a metallocene catalyst.

Another object of the present invention is to provide a container decorated with the label.

Figure 1:
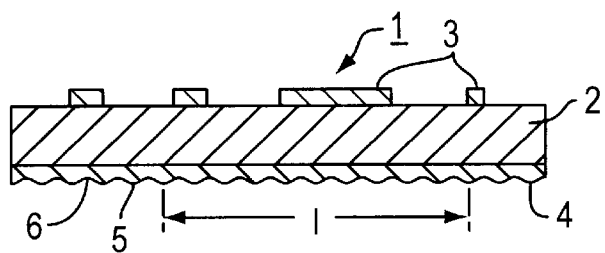
FIG. 1 is a sectional view of an in-mold label.

Description of the Symbols used in the Figure
1: label
2: thermoplastic resin film base layer (I)
3: printed matter
4: heat sealable resin layer (II)
5: top of embossed pattern
6: valley of embossed pattern

DETAILED DESCRIPTION OF THE INVENTION

Structure of the In-mold Label

The in-mold label of the present invention is now described in detail.

FIG. 1 is a sectional view of an in-mold label for blow molding. In the figure, numeral 1 denotes the label, 2 a thermoplastic resin film base layer (I), 3 printed matter, and 4 a heat sealable resin layer (II). If desired and necessary, the heat sealable resin layer (II) may be embossed to avoid label blistering after application to a container (see U.S. Pat. No. 4,986,866 and JP-A-3-260689). Numeral 5 denotes the top of an embossed pattern and 6 denotes a valley thereof.

Figure 2:
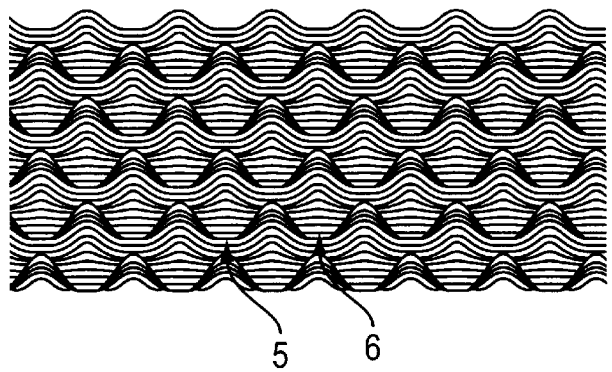
FIG. 2 is an enlarged plan view of the in-mold label of FIG. 1, viewed from the back side which shows the results of measurement with a surface roughness meter.
Figure 3:
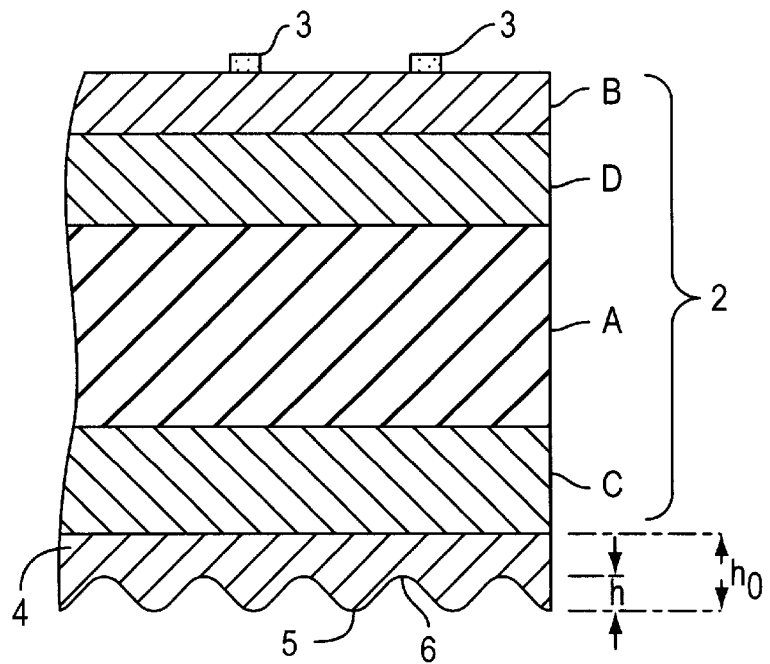
FIG. 3 is an enlarged sectional view of part of the in-mold label of FIG. 1.

FIG. 2 is a plan view of the label 1, viewed from the side of the heat sealable resin layer 4 (from the back side of the label). FIG. 3 is an enlarged sectional view of part of the label.

FIGS. 4, 5, 6, 7 and 8 are differential and integral elution curves.

Figure 9:
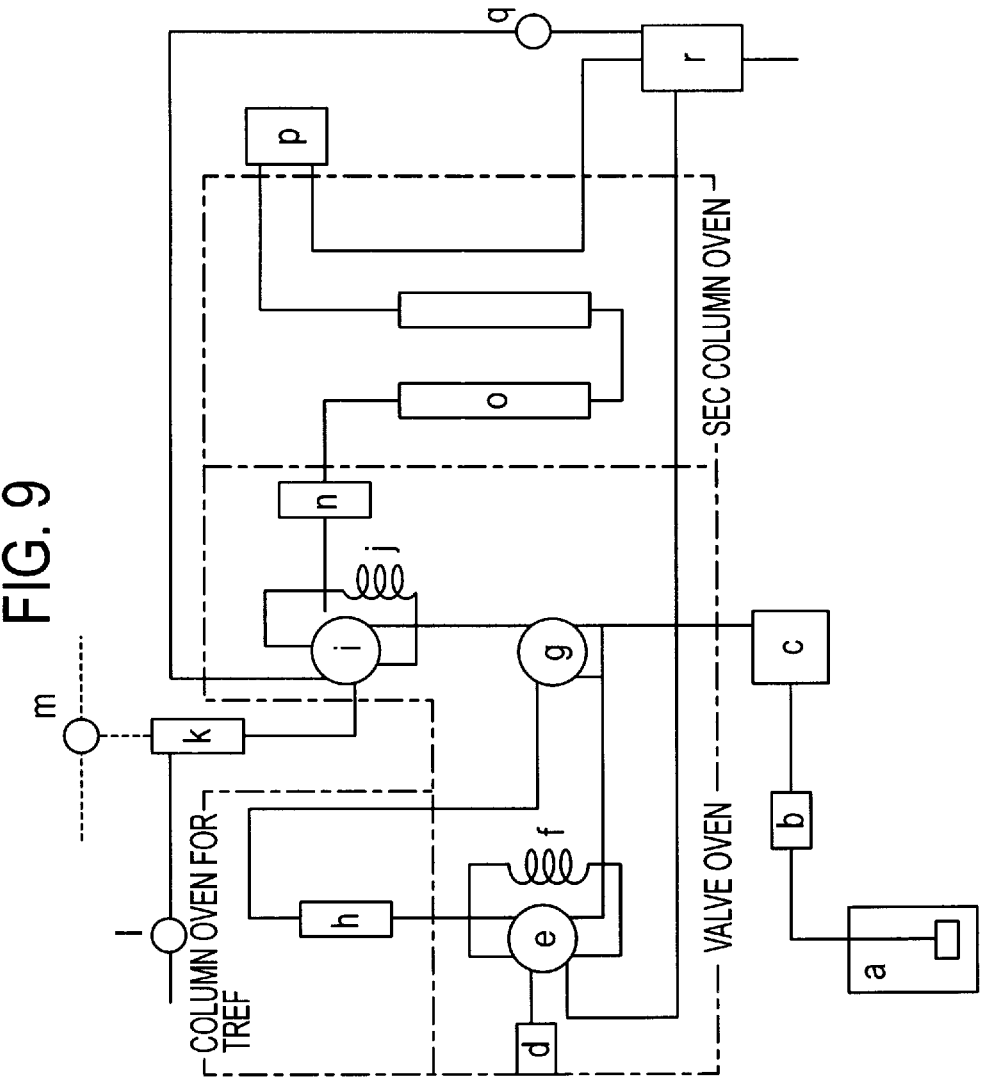
FIG. 9 is a flow sheet illustrating an apparatus for use in the temperature rising elution fractionation (TREF) of resins (i.e., a crystallizability fractionation device).

FIG. 9 is a crystallizability fractionation device. Base Layer Film (I)

The label base layer (I) can be a thermoplastic resin layer as is conventionally used as a label base. Examples thereof include a resin film having a melting point of from 135° to 264° C., e.g., polypropylene, high density polyethylene, poly(vinyl chloride), poly(ethylene terephthalate), or a polyamide; a synthetic paper obtained by stretching a polypropylene film containing from 8 to 65 wt % inorganic filler as disclosed in U.S. Pat. No. 4,318,950; a coated film obtained by coating the above-described resin film or synthetic paper with a latex containing an inorganic filler (coating material); a base comprising a vapor deposited aluminum layer formed on any of the above described films; and a laminate of any of the above described films with an aluminum foil.

Preferred of such examples of the base layer (I) from the standpoints of printability, suitability for label feeding into molds, and prevention of thermal shrinkage is a microporous laminate resin film comprising a biaxially stretched film base layer (A) comprising from 5 to 30 wt % fine inorganic particles, from 3 to 20 wt % high density polyethylene, and from 92 to 50 wt % polypropylene resin, a paper-like layer (B) made of a uniaxially stretched film of a resin composition comprising from 35 to 65 wt % fine inorganic particles, from 0 to 10 wt % high density polyethylene, and from 55 to 35 wt % polypropylene resin, and a paper-like layer (C) made of a uniaxially stretched film of a resin composition comprising from 35 to 65 wt % fine inorganic particles, from 0 to 10 wt % high density polyethylene, and from 55 to 35 wt % polypropylene resin.

The paper-like (B) is laminated to one side of the base layer (A) and the paper-like layer (C) is laminated to the base layer (A) on the side opposite to the paper-like layer (B).

The thickness of the base layer (A) is preferably from 30 to 150 μm, and the thickness of the paper layer (B) and (C) is each from 0.5 to 40 μm.

Preferred examples of the base layer (I) further include a base layer film having a layer for density regulation formed between the above-described base layer (A) and paper-like layer (B). Specifically, this type of base layer is, for example, a microporous laminate resin film comprising a biaxially stretched film base layer (A) comprising from 5 to 30 wt % fine inorganic particles, from 3 to 20 wt % high density polyethylene, and from 92 to 50 wt % polypropylene resin, a paper-like layer (C) made of a uniaxially stretched film of a resin composition comprising from 35 to 65 wt % fine inorganic particles, from 0 to 10 wt % high density polyethylene, and from 55 to 35 wt % polypropylene resin, an interlayer (D) laminated to the base layer (A) on the side opposite to the paper-like layer (C) made of a uniaxially stretched film of a resin composition comprising from 35 to 65 wt % fine inorganic particles, from 0 to 10 wt % high density polyethylene and from 55 to 35 wt % polypropylene resin, and a paper-like layer (B) made of a uniaxially stretched film of a resin composition comprising from 35 to 65 wt % fine inorganic particles, from 0 to 10 wt % high density polyethylene, and from 55 to 35 wt % polypropylene resin. The paper-like layer (B) is laminated to the interlayer (D) and is different from the interlayer (D) with respect to the content of the fine inorganic particles therein.

The paper like layer (B) contains from 3 to 35 wt % more fine inorganic particles than those in the interlayer (D).

Either of these types of microporous stretched laminate resin films, i.e., with or without interlayer (D), have a density of from 0.65 to 1.02 g/cm$^3$ and a porosity of 5 to 55%, preferably 15 to 45%. In these microporous stretched laminate resin films (I), printed material is formed on the paper-like layer (B) side and a heat sealable resin layer (II) is formed on the paper-like layer (C) side.

The thickness of the base layer (I) is from 20 to 200 μm, preferably from 40 to 150 μm.

Heat Sealable Resin Layer (II)

The heat sealable resin layer (II) comprises as the main component an ethylene/α-olefin copolymer obtained by copolymerizing from 40 to 98 wt % ethylene and from 60 to 2 wt % of an α-olefin (total: 100 wt %) having from 3 to 30 carbon atoms using a metallocene catalyst.

This ethylene/α-olefin copolymer preferably satisfies the following property requirements (1), (2) and (3):

(1) it has an MFR (190° C., 2.16 kg load) of from 2 to 30 g/10 min;

(2) it has a density of 0.860 to 0.935 g/cm$^3$; and (3) in temperature rising elution fractionation (TREF), it gives an elution curve which has one peak, in which the peak temperature is from 20° to 85° C. and the value of H/W, where H is the height of the peak and W is the peak width at half height, is 1 to 3, and which shows that the copolymer contains one or more components which are eluted at a temperature other than the peak elution temperature.

An especially preferred material of the heat sealable resin layer (II) is a resin composition comprising:

(a) from 50 to 90 wt % ethylene/α-olefin copolymer satisfying the above-described property requirements (1), (2), and (3); and (b) from 50 to 10 wt % (so as to total 100 wt %) high pressure low density polyethylene satisfying the following property requirements (1'), (2'), (3'), and (4'):

(1') it has an MFR (JIS K7210; 190° C., 2.16 kg) of from 0.1 to 20 g/10 min;

(2') it has a density (JIS K7112) of from 0.915 to 0.93 g/cm$^3$;

(3') it has a memory effect (ME) of 1.6 to 3; and (4') it has a melt tension (MT) of 1.5 g to 15 g.

The ethylene/α-olefin copolymer of ingredient (a), which is a type of a linear low density polyethylene, is obtained by copolymerizing a major proportion of ethylene and a minor proportion of an α-olefin using a metallocene catalyst. Examples of the catalyst include metallocene/aluminoxane catalysts and catalysts comprising a combination of a metallocene compound (such as that disclosed in, e.g., International Publication WO 92/01723) and a compound of the formula MI$_x$ (hereinafter described) which reacts with the metallocene compound to change such compound into a stable anion.

Ethylene is used in a proportion of from 40 to 98 wt %, preferably from 50 to 95 wt %, and most preferably from 70 to 93 wt %, balance α-olefin so as to total 100 wt %.

Examples of the α-olefin having from 3 to 30 carbon atoms which is copolymerized with ethylene include propylene, 1-butene, 1-pentene, 1-hexene, 1-octene, 1-heptene, 4-methylpentene-1, 4-methylhexene-1, 4,4-dimethylpentene-1, and octadecene. Preferred of these are 1-hexene, 1-octene, 1-heptene, and 4-methylpentene-1.

The α-olefin is used in a proportion of from 2 to 60 wt %, preferably from 5 to 50 wt %, and most preferably from 7 to 30 wt %.

Examples of the metallocene catalyst further include metallocene compounds represented by the following formula.

In the formula, M is a transition metal selected from the group consisting of Zr, Ti, Hf, V, Nb, Ta, and Cr; each L is a ligand coordinated to the transition metal, at least one of which is a ligand having a cyclopentadienyl skeleton, with the balance (if any) being a hydrocarbon group having from 1 to 12 carbon atoms, an alkoxy group, an aryloxy group, a trialkylsilyl group, an SO$_3$R group (where R is a hydrocarbon group having from 1 to 8 carbon atoms and optionally substituted with, e.g., a halogen), a halogen atom, or a hydrogen atom; and x is the valence of the transition metal.

Examples of the ligand having a cyclopentadienyl skeleton include a cyclopentadienyl group, alkyl-substituted cyclopentadienyl groups such as methylcyclopentadienyl, dimethylcyclopentadienyl, trimethylcyclopentadienyl, tetramethylcyclopentadienyl, pentamethylcyclopentadienyl, ethylcyclopentadienyl, methylethylcyclopentadienyl, propylcyclopentadienyl, methylpropylcyclopentadienyl, butylcyclopentadienyl, methylbutylcyclopentadienyl, and hexylcyclopentadienyl; an indenyl group; a 4,5,6,7-tetrahydroindenyl group; and a fluorenyl group. These groups may be substituted with a halogen atom such as F, Cl and Br, a trialkylsilyl group, etc.

Especially preferred of these ligands coordinated to the transition metal are alkyl-substituted cyclopentadienyl groups. In the case where the compounds represented by the above described general formula have two or more groups each having a cyclopentadienyl skeleton, two of these groups may be bonded to each other through an alkylene group, e.g., ethylene or propylene, a substituted alkylene group, e.g., isopropylidene or diphenylmethylene, a silylene group, a substituted silylene group, e.g., dimethylsilylene, diphenylsilylene or methylphenylsilylene.

Examples of the ligands other than the ligands having a cyclopentadienyl skeleton include the following. Examples of the hydrocarbon group having from 1 to 12 carbon atoms include alkyl groups, cycloalkyl groups, aryl groups and aralkyl groups. Examples of the alkyl groups include methyl, ethyl, propyl, isopropyl and butyl. Examples of the cycloalkyl groups include cyclopentyl and cyclohexyl. Examples of the aryl groups include phenyl and tolyl. Examples of the aralkyl groups include benzyl and neophyl. Examples of the alkoxy groups include methoxy, ethoxy and butoxy. Examples of the aryloxy groups include phenoxy. Examples of the halogen include fluorine, chlorine, bromine and iodine.

Examples of the ligand represented by $SO_3R$ include a p-toluenesulfonato group, a methanesulfonato group, and a trifluoromethanesulfonato group.

The above-described metallocene compounds containing at least one ligand having a cyclopentadienyl skeleton can be more specifically represented by the following formula, in the case where the transition metal has a valence of, for example, 4.

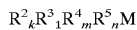

$$R^2_k R^3_l R^4_m R^5_n M$$

In the formula, M is the transition metal as earlier described; $R^2$ is a group (ligand) having a cyclopentadienyl skeleton as earlier described; $R^3$, $R^4$, and $R^5$ each is a group having a cyclopentadienyl skeleton as earlier described, or an alkyl group, a cycloalkyl group, an aryl group, an aralkyl group, an alkoxy group, an aryloxy group, a trialkylsilyl group, an $SO_3R$ group, a halogen atom or a hydrogen atom as earlier described; k is an integer of 1 or larger; and k+l+m+n=4.

Preferred metallocene compounds for use in the present invention are represented by the above formula $R^2_k R^3_l R^4_m R^5_n M$ where at least two of $R^2$, $R^3$, $R^4$, and $R^5$, i.e., $R^2$ and $R^3$, each is a group (ligand) having a cyclopentadienyl skeleton. These groups having a cyclopentadienyl skeleton may be bonded to each other through an alkylene group, e.g., ethylene or propylene, a substituted alkylene group, e.g., isopropylidene or diphenylmethylene, a silylene group, a substituted silylene group, e.g., dimethylsilylene, diphenylsilylene or methylphenylsilylene, or another group. $R^4$ and $R^5$ each is a group having a cyclopentadienyl skeleton, or an alkyl group, a cycloalkyl group, an aryl group, an aralkyl group, an alkoxy group, an aryloxy group, a trialkylsilyl group, $SO_3R$, a halogen atom or a hydrogen atom.

Specific examples of transition metal compounds wherein M is zirconium include bis(indenyl)zirconium dichloride, bis(indenyl)zirconium dibromide, bis(indenyl)zirconium bis(p-toluenesulfonate), bis(4,5,6,7-tetrahydroindenyl) zirconium dichloride, bis(fluorenyl)zirconium dichloride, ethylenebis(indenyl)zirconium dichloride, ethylenebis(indenyl)zirconium dibromide, ethylenebis(indenyl)dimethylzirconium, ethylenebis(indenyl)diphenylzirconium, ethylenebis(indenyl)methylzirconium monochloride, ethylenebis(indenyl)zirconium bis(methanesulfonate), ethylenebis(indenyl)zirconium bis(p-toluenesulfonate), ethylenebis(indenyl)zirconium bis(trifluoromethanesulfonate), ethylenebis(4,5,6,7-tetrahydroindenyl)zirconium dichloride, isopropylidene (cyclopentadienylfluorenyl)zirconium dichloride, isopropylidene(cyclopentadienylmethylcyclopentadienyl) zirconium dichloride, dimethylsilylenebis (cyclopentadienyl)zirconium dichloride, dimethylsilylenebis(methylcyclopentadienyl)zirconium dichloride, dimethylsilylenebis(dimethylcyclopentadienyl) zirconium dichloride, dimethylsilylenebis (trimethylcyclopentadienyl)zirconium dichloride, dimethylsilylenebis(indenyl)zirconium bis (trifluoromethanesulfonate), dimethylsilylenebis(4,5,6,7-tetrahydroindenyl)zirconium dichloride, dimethylsilylenebis(cyclopentadienylfluorenyl)zirconium dichloride, diphenylsilylenebis(indenyl)zirconium dichloride, methylphenylsilylenebis(indenyl)zirconium dichloride, bis(cyclopentadienyl)zirconium dichloride, bis (cyclopentadienyl)zirconium dibromide, bis (cyclopentadienyl)methylzirconium monochloride, bis (cyclopentadienyl)ethylzirconium monochloride, bis (cyclopentadienyl)cyclohexylzirconium monochloride, bis (cyclopentadienyl)phenylzirconium monochloride, bis (cyclopentadienyl)benzylzirconium monochloride, bis (cyclopentadienyl)zirconium monochloride monohydride, bis(cyclopentadienyl)methylzirconium monohydride, bis (cyclopentadienyl)dimethylzirconium, bis (cyclopentadienyl)diphenylzirconium, bis (cyclopentadienyl)dibenzylzirconium, bis (cyclopentadienyl)zirconium methoxy chloride, bis (cyclopentadienyl)zirconium ethoxy chloride, bis (cyclopentadienyl)zirconium bis(methanesulfonate), bis (cyclopentadienyl)zirconium bis(p-toluenesulfonate), bis (cyclopentadienyl)zirconium bis (trifluoromethanesulfonate), bis(methylcyclopentadienyl) zirconium dichloride, bis(dimethylcyclopentadienyl) zirconium dichloride, bis(dimethylcyclopentadienyl) zirconium ethoxy chloride, bis(dimethylcyclopentadienyl) zirconium bis(trifluoromethanesulfonate), bis (ethylcyclopentadienyl)zirconium dichloride, bis (methylethylcyclopentadienyl)zirconium dichloride, bis (propylcyclopentadienyl)zirconium dichloride, bis (methylpropylcyclopentadienyl)zirconium dichloride, bis (butylcyclopentadienyl)zirconium dichloride, bis (methylbutylcyclopentadienyl)zirconium dichloride, bis (methylbutylcyclopentadienyl)zirconium bis (methanesulfonate), bis(trimethylcyclopentadienyl) zirconium dichloride, bis(tetramethylcyclopentadienyl) zirconium dichloride, bis(pentamethylcyclopentadienyl) zirconium dichloride, bis(hexylcyclopentadienyl)zirconium dichloride and bis(trimethylsilylcyclopentadienyl)zirconium dichloride.

In the compounds enumerated above, the disubstituted cyclopentadienyl rings include 1,2-substituted and 1,3-substituted rings, while the trisubstituted cyclopentadienyl rings include 1,2,3-substituted and 1,2,4-substituted rings. The alkyl groups such as propyl and butyl include n-, i-, sec-, tert-, and other isomers.

Also usable are compounds having the same structures as the above-enumerated zirconium compounds except that the zirconium atom has been replaced with a titanium, hafnium, vanadium, niobium, tantalum or chromium atom. All of these compounds may be used alone or as a combination of two or more thereof. They may be diluted with a hydrocarbon or a halogenated hydrocarbon before use. In the present invention, the metallocene compound is preferably a zirconocene compound in which the central metal atom is zirconium and which has at least two ligands each having a cyclopentadienyl skeleton.

Examples of the aluminoxane used in combination with the metallocene compound include aluminoxanes represented by general formulae (1) and (2).

  (1)

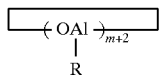  (2)

In formulae (1) and (2), R is a hydrocarbon group, e.g., methyl, ethyl, propyl, or butyl, preferably methyl or ethyl, and more preferably methyl, and m is an integer of 2 or larger, preferably from 5 to 40.

The aluminoxane may comprise mixed alkyloxyaluminum units consisting of one or more alkyloxyaluminum units represented by the formula $(OAl(R^1))$ and one or more alkyloxyaluminum units represented by the formula $(OAl(R^2))$, where $R^1$ and $R^2$ each is a hydrocarbon group, examples of which are the same as those given with regard to R, provided that $R^1$ and $R^2$ represent different groups. In this case, the aluminoxane desirably comprises mixed alkyloxyaluminum units containing one or more methyloxyaluminum units $(OAl(CH_3))$ in an amount of 30 mol % or larger, preferably 50 mol % or larger, especially preferably 70 mol % or larger.

For producing such an aluminoxane, the following methods can, for example, be used.

(1) A method in which an organoaluminum compound, e.g., a trialkylaluminum, is added to a suspension in a hydrocarbon medium of either a compound having adsorbed water or a salt having water of crystallization, e.g., magnesium chloride hydrate, copper sulfate hydrate, aluminum sulfate hydrate, nickel sulfate hydrate, or cerous chloride hydrate, to thereby react the organoaluminum compound with the water.

(2) A method in which an organoaluminum compound, e.g., a trialkylaluminum, is directly reacted with water in various media, e.g., benzene, toluene, ethyl ether, or tetrahydrofuran.

(3) A method in which an organoaluminum compound, e.g., a trialkylaluminum, is reacted with an organotin compound, e.g., dimethyltin oxide or dibutyltin oxide, in various media, e.g., decane, benzene, or toluene.

Of these methods, method (1) is preferably employed. The aluminoxane may contain a small amount of organometallic ingredients other than aluminum compounds. After the solvent or the unreacted organoaluminum compound is removed by distillation from the recovered aluminoxane solution, the aluminoxane may be redissolved in a solvent such as a hydrocarbon or halogenated hydrocarbon.

Examples of the organoaluminum compound used for producing an aluminoxane include trialkylaluminums such as trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, trihexylaluminum, trioctylaluminum and tridecylaluminum; tricycloalkylaluminums such as tricyclohexylaluminum and tricyclooctylaluminum; dialkylaluminum halides such as dimethylaluminum chloride, diethylaluminum chloride, diethylaluminum bromide and diisobutylaluminum chloride; dialkylaluminum hydrides such as diethylaluminum hydride and diisobutylaluminum hydride; dialkylaluminum alkoxides such as dimethylaluminum methoxide and diethylaluminum ethoxide; and dialkylaluminum aryloxides such as diethylaluminum phenoxide.

Also usable as the organoaluminum compound are isoprenylaluminums represented by the following formula.

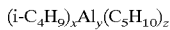

In the formula, x, y, and z each is a positive number, and $z \geq 2x$.

Especially preferred of the above enumerated organoaluminum compounds are trialkylaluminums.

The organoaluminum compounds enumerated above may be used alone or in combination.

Examples of the solvent or media used for producing an aluminoxane include aromatic hydrocarbons such as benzene, toluene, xylene, cumene and cymene; aliphatic hydrocarbons such as pentane, hexane, heptane, octane, decane, dodecane, hexadecane and octadecane; alicyclic hydrocarbons such as cyclopentane, cyclohexane, cyclooctane and methylcyclopentane; petroleum fractions such as gasoline, kerosene and gas oil; halides, in particular chlorides and bromides, of the above enumerated aromatic, aliphatic, and alicyclic hydrocarbons; and ethers such as ethyl ether and tetrahydrofuran. Especially preferred of these are aromatic hydrocarbons.

The proportion of the aluminum contained in the aluminoxane to all of the metal contained in the metallocene is about from 0.5:1 to 10,000:1, preferably about from 5:1 to 1,000:1.

The compound which reacts with a metallocene compound to change the compound into a stable anion is either an ionic compound made up of a cation and an anion or an electrophilic compound. Upon reaction with the metallocene compound, the ionic or electrophilic compound changes into a stable ion to form an active species which catalyzes polymerization.

Specifically, the ionic compound is represented by the following formula.

In the formula, Q is the cation component of the ionic compound, examples of which include a carbonium cation, a tropylium cation, an ammonium cation, an oxonium cation, a sulfonium cation and a phosphonium cation. Examples of the cation component further include metallic and organometallic cations which themselves are susceptible to reduction.

These cations may be cations capable of yielding protons such as those disclosed in JP-W-1-501950 (the term "JP-W" as used herein means an "unexamined published Japanese patent application based on an international patent application), or may be cations which do not yield protons. Specific examples of such cations include triphenylcarbonium, diphenylcarbonium, cycloheptatrienium, indenium, triethylammonium, tripropylammonium, tributylammonium, N,N-dimethylanilinium, dipropylammonium, dicyclohexylammonium, triphenylphosphonium, trimethylphosphonium, tri(dimethylphenyl)phosphonium, tri(methylphenyl)phosphonium, triphenylsulfonium, triphenyloxonium, triethyloxonium, pyrylium, silver ion, gold ion, platinum ion, palladium ion, mercury ion and ferrocenium ion.

Y is the anion component of the ionic compound. It changes into a stable anion upon reaction with a metallocene compound. Examples of the anion include organoboron compound anions, organoaluminum compound anions, organogallium compound anions, organphosphorus compound anions, organoarsenic compound anions, and organoantimony compound anions. Specific examples thereof include tetraphenylboron, tetrakis(3,4,5-trifluorophenyl)boron, tetrakis(3,5-di(trifluoromethyl)phenyl)boron, tetrakis(pentafluorophenyl)boron, tetraphenylaluminum, tetrakis(3,4,5-trifluorophenyl)aluminum, tetrakis(3,5-di(trifluoromethyl)phenyl)aluminum, tetrakis(pentafluorophenyl)aluminum, tetraphenylgallium, tetrakis(3,4,5-trifluorophenyl)gallium, tetrakis(3,5-di(trifluoromethyl)phenyl)gallium, tetrakis(3,5-di(t-butyl)phenyl)gallium, tetrakis(pentafluorophenyl)gallium, tetraphenylphosphorus, tetrakis(pentafluorophenyl)phosphorus, tetraphenylarsenic, tetrakis(pentafluorophenyl)arsenic, tetraphenylantimony, tetrakis(pentafluorophenyl)antimony, decaborate, undecaborate, carbadodecaborate and decachlorodecaborate.

m is a cardinal number such as 1, 2, 3, 4, etc., of the ion value of Q and Y.

The electrophilic compound is a compound which is known as a Lewis acid and it reacts with a metallocene compound to change the electrophilic compound into a stable anion and form an active species which catalyzes polymerization. Examples of the electrophilic compound include various metal halide compounds and metal oxides known as solid acids. Specific examples thereof include magnesium halides such as $MgCl_2$ and inorganic compounds known as Lewis acids.

Examples of polymerization methods useful herein include vapor phase polymerization, slurry polymerization, solution polymerization and high pressure ionic polymerization. Preferred of these are solution polymerization and high pressure ionic polymerization. In particular, the high pressure ionic polymerization process is preferably used for polymer production.

Examples of this high pressure ionic polymerization process include the continuous process for ethylene polymer production described in JP-A-56-18607 and JP-A-58-225106, in which polymerization is conducted under the reaction conditions of a pressure of 100 kg/cm² or higher, preferably from 200 to 2,000 kg/cm², and a temperature of 125° C. or higher, preferably from 130° to 250° C. and more preferably from 150° to 200° C.

Preferred of the ethylene/α-olefin copolymers obtained with such metallocene catalysts is an ethylene/α-olefin copolymer which is obtained with a catalyst comprising a combination of a metallocene compound and an ionic compound represented by the earlier described formula

and which satisfies the following property requirements (1) to (3) and preferably further satisfies the property requirements (4) and (5).

(1) MFR

To have an MFR (melt flow rate) as measured in accordance with JIS K7210 of from 2 to 30 g/10 min, preferably from 5 to 25 g/10 min, more preferably from 10 to 22 g/10 min, and most preferably from 13 to 20 g/10 min.

Copolymers having an MFR higher than the upper limit show unstable film formation, while copolymers having an MFR lower than the lower limit suffer film breakage during molding.

(2) Density

To have a density as measured in accordance with JIS K7112 of 0.860 to 0.935 g/cm³, preferably from 0.87 to 0.92 g/cm³, more preferably from 0.88 to 0.913 g/cm³, and most preferably from 0.89 to 0.91 g/cm³.

Copolymers having a density higher than the upper limit have poor low temperature heat sealability, while copolymers having too low a density give films which have surface tackiness and are unable to be put to practical use. The lower limit of the density is usually about 0.86 g/cm³.

(3) Peak Temperature of Elution Curve obtained in Temperature Rising Elution Fractionation In temperature rising elution fractionation (TREF), the ethylene/α-olefin copolymer gives an elution curve which has one peak, where the peak temperature is from 20° to 85° C., preferably from 30° to 75° C., most preferably from 40° to 70° C., and the value of [the peak height]/[the peak width at half height] (H/W) is 1 or more, preferably from 1 to 20, more preferably from 1 to 15, and most preferably from 1 to 10.

Figure 4:
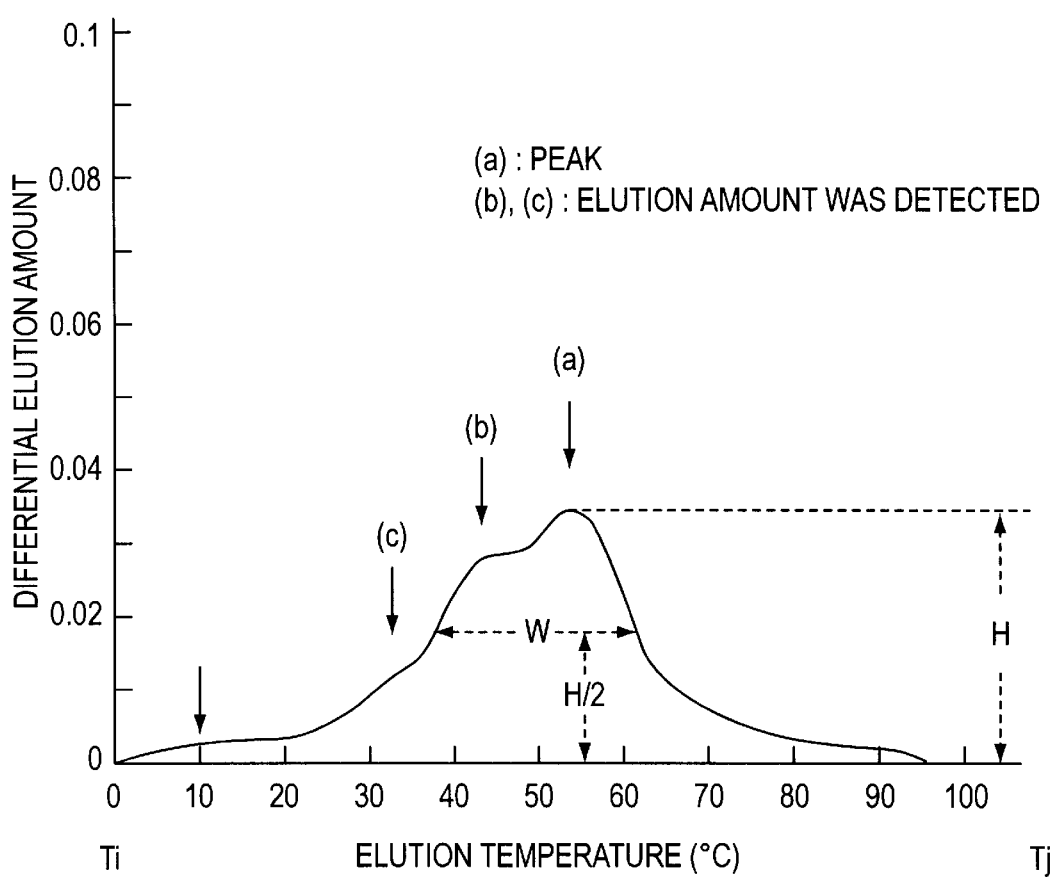
FIG. 4 shows a TREF curve.
Figure 5:
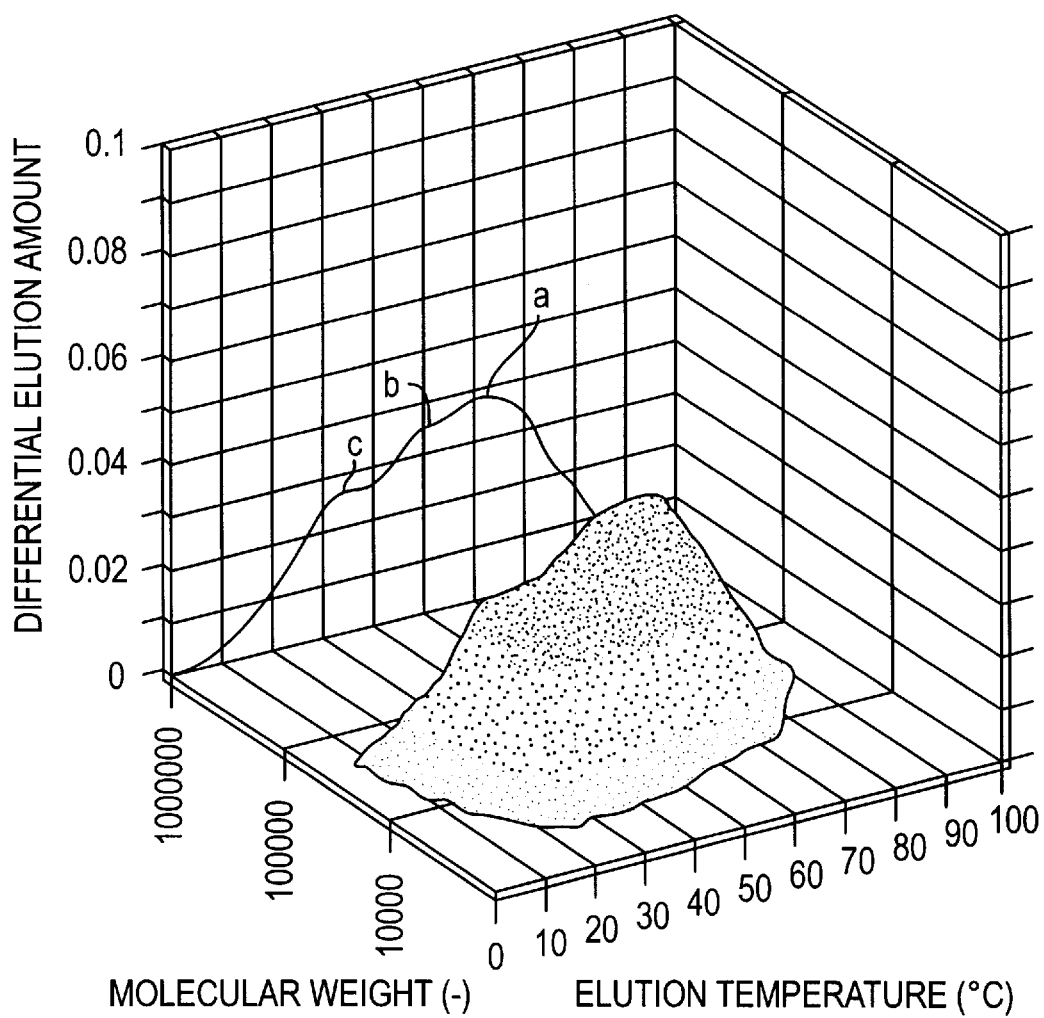
FIGS. 5, 6, 7 and 8 are differential and integral elution curves.
Figure 6:
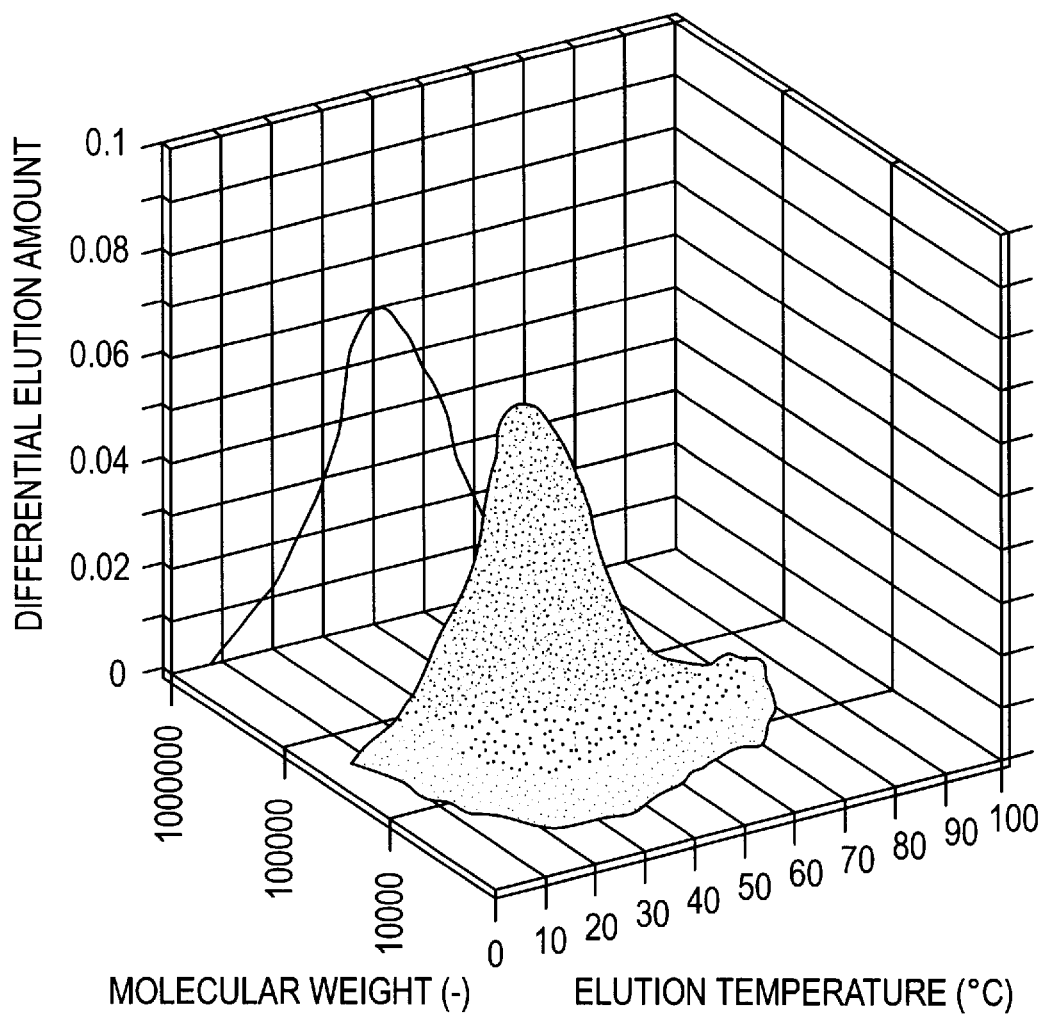

The word "one peak" as used herein means one projecting portion in the figure drawn as a bird's-eye view as shown in FIG. 5 or 6. Such a projecting portion may have small projecting portions b, c with easy or gradual undulations as shown in FIG. 5. The elution curve may show that the copolymer contains one or more components which are eluted at a temperature other than the peak elution temperature (see FIG. 4, (b) and (c), and FIG. 5).

Figure 7:
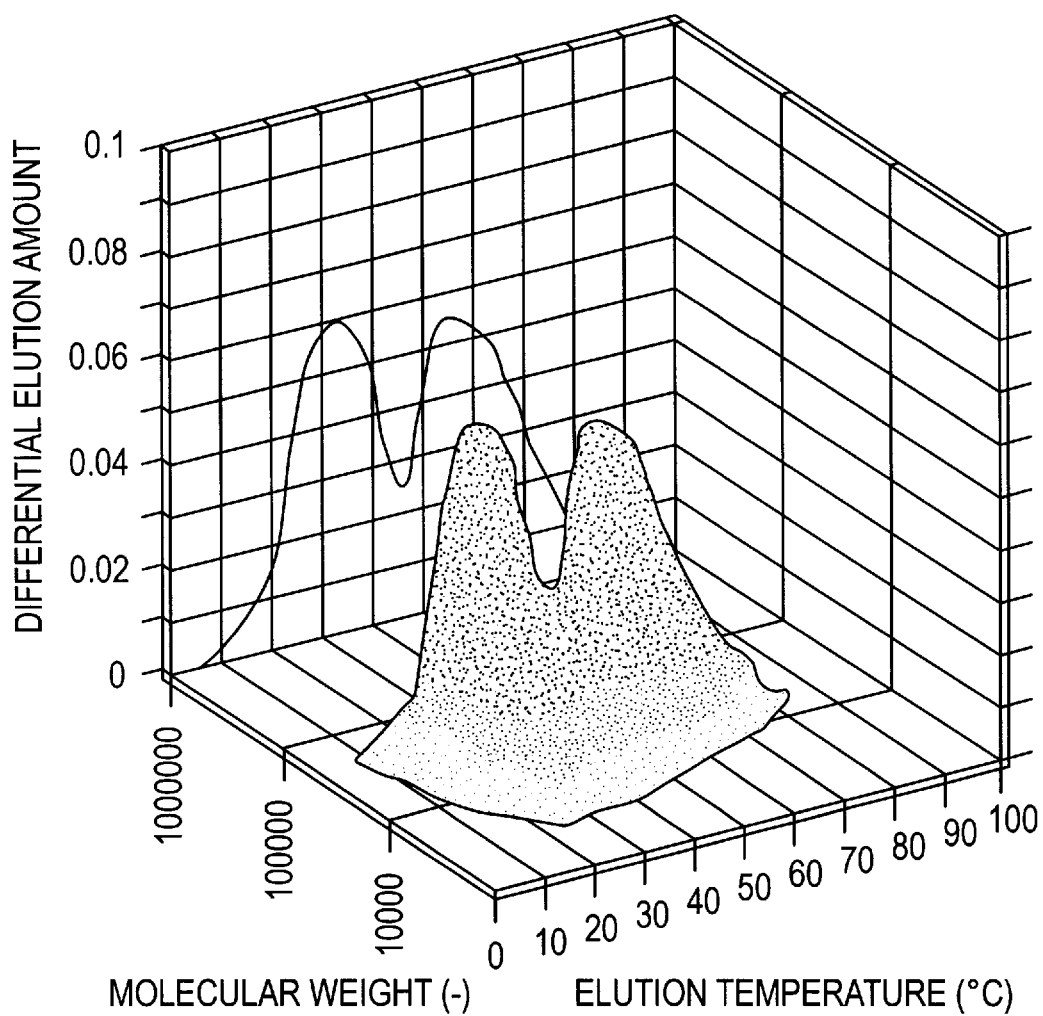
Figure 8:
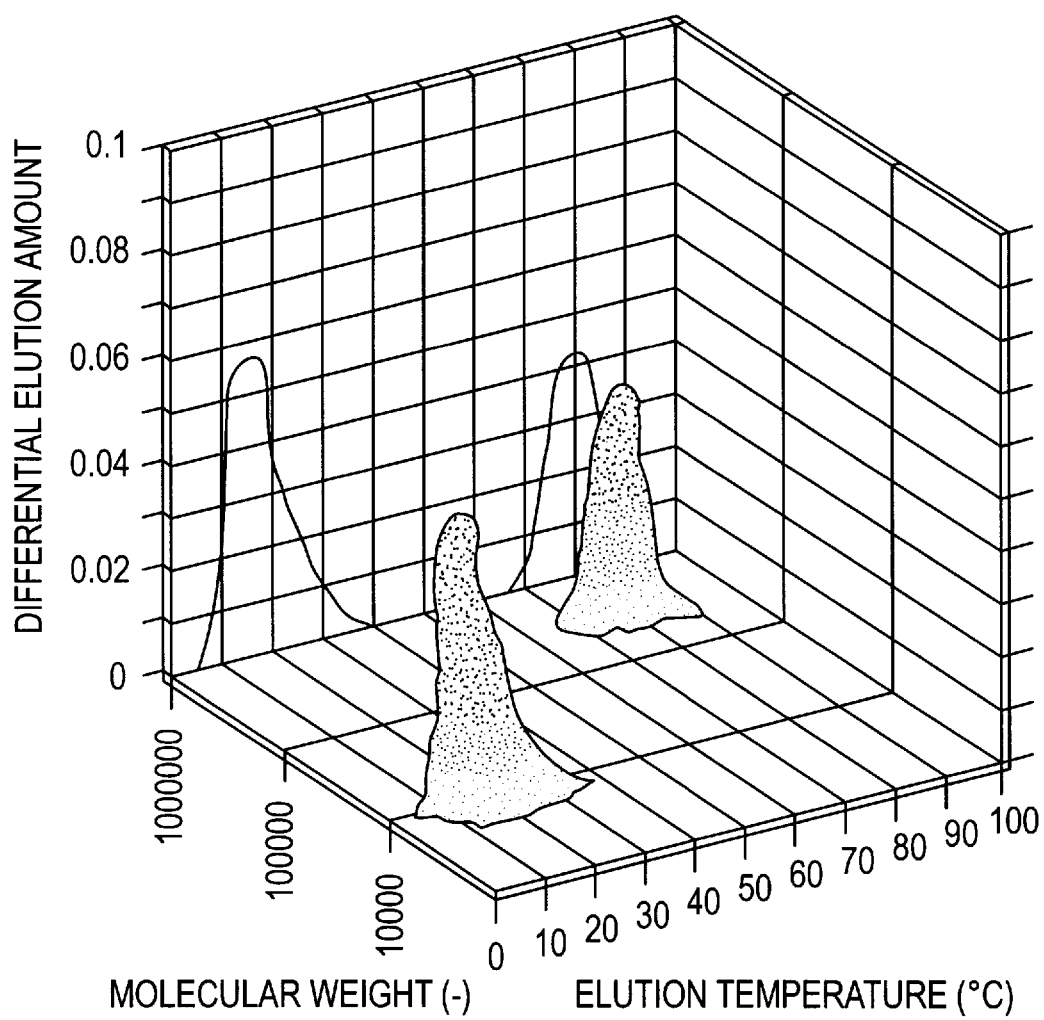

A projecting portion, comprising two peaks and a valley therebetween as shown in FIG. 7, and a pair of projecting portions, completely separated from each other, however, fall outside the scope of the definition of the word "one peak".

If the peak temperature of the elution curve exceeds the upper limit, the copolymer has poor low temperature heat sealability and is hence unsuitable for practical use.

If the value of H/W is below the lower limit, the copolymer comes to have poor heat sealability with the passage of time due to a large proportion of tacky components contained therein and is hence unsuitable for practical use.

Determination of Elution Curve through Temperature Rising Elution Fractionation

The temperature rising elution fractionation for determining an elution curve is carried out according to *Journal of Applied Polymer Science*, Vol. 26, pp. 4217–4231 (1981), hereby incorporated by reference. In this analysis, a cross fractionator is used which has three independent ovens [a column oven for TREF (packed with glass beads heated to 140° C.), a valve oven, and an SEC column oven] as shown in FIG. 9. The ethylene resin to be analyzed is dissolved in a solvent, e.g., o-dichlorobenzene, with heating (140° C.), and this resin solution is injected into a sample loop (f) through a sample valve (e) with a syringe (d). Upon pushing an analysis initiation switch, the analysis is automatically carried out.

An injection valve (g) is operated first, followed by operation of a sample valve (e). After a given volume (0.5 ml) of the solution has been injected into the sample loop (f), the sample valve (e) recovers its original position, and the solution in the sample loop is introduced into the center of a TREF column (h), whereupon the injection valve (g) returns to its original position. The TREF column is cooled from 140° C. to 0° C. at a rate of 1° C./min, and the resin deposits on the surface of the carrier (glass beads) packed in the column (this polymer layer deposition on the glass bead surface occurs in the range from highly crystalline (high elution temperature) components to slightly crystalline (low elution temperature) components). After the TREF column is cooled to 0° C., it is maintained at this temperature for a given period (30 minutes). Any resin component which is in a dissolved state at that temperature is sent from the TREF column to an SEC column at a flow rate of 1 ml/min by operating the injection valve (g). Thereafter, molecular sieve fractionation is conducted in the SEC column, during which the TREF column is gradually heated from 0° to 140° C., while being maintained at each of the following temperatures for 30 minutes.

Temperature (°C.): 0, 5, 10, 15, 20, 25, 30, 35, 40, 45, 49, 52, 55, 58, 61, 64, 67, 70, 73, 76, 79, 82, 85, 88, 91, 94, 97, 100, 102, 120, 140

During the above procedure, the TREF column is heated to the next predetermined temperature and maintained at this temperature, during which time the molecular sieve fractionation of the resin solution which has been injected into the SEC column is conducted in the column (the analysis of each elution fraction in the SEC column is performed at an interval of 39 minutes). Data regarding a chromatogram are stored in a computer.

The solution separated is analyzed with an infrared detector (p) to determine the resin concentration. Thereafter, the injection, heating, and molecular sieve fractionation are repeated.

In FIG. 9, (a) denotes a solvent tank, (b) an auxiliary pump, (c) a pump, (d) a syringe, (e) a six-way sample valve, (f) a sample loop, (g) an injection valve, (h) a TREF column, (i) a six-way valve, (j) an initial standard solution loop, (k) a tank, (1 ) a stop valve, (m) a three-way valve, (n) an internal filter, (o) an SEC column, (p) an infrared detector, (q) a stop valve, and (r) a waste liquid tank.

Since an internal standard solution is injected at a predetermined time period after the injection of the resin solution, it does not influence the separation of lower molecular components.

The data stored in the computer are processed and outputted as differential and integral elution curve (see FIG. 4).

Specifically, using built-in data processing software, a base line of the chromatogram for each elution temperature obtained in the above analysis is drawn, and arithmetic processing is conducted. The area of each chromatogram is integrated to calculate an integral elution curve. This integral elution curve is differentiated with temperature to calculate a differential elution curve. The results of these calculations are outputted with a printer to obtain a differential and integral elution curve, in which the elution temperature is plotted as the abscissa, with 89.3 mm being used per elution temperature range of 100° C., and the differential amount (the total integral elution amount being standardized as 1.0 and the rate of change per 1° C. being taken as the differential amount) is plotted as the ordinate, with 76.5 mm being used per differential amount range of 0.1. The value obtained by dividing the peak height (mm) of this differential elution curve by the peak width (mm) at half height is referred to as H/W. In FIG. 4, H/W is 38/30.

In this TREF curve, non-crystalline components of the ethylene resin, i.e., ethylene resin components having a high degree of branching of short branch chains, dissolve first in a low temperature range. As the elution temperature rises, components having a lower degree of branching gradually dissolve. Finally, linear ethylene resin components having no branches dissolve, whereupon the analysis is terminated.

In the Examples of the present invention, a cross fractionator CFCT150A (trade name), manufactured by the Mitsubishi Chemical Corporation, was used, in which the TREF column was packed with glass beads as an inactive carrier. The SEC column used was composed of three AD80M/S (trade name) columns, manufactured by Showa Denko K.K., arranged in series and packed with a polystyrene gel.

The resin solution to be injected into the sample loop (f) of the cross fractionator was prepared by dissolving the ethylene resin in o-dichlorobenzene in such an amount as to result in a resin concentration of 4 mg/ml, and was injected in an amount of 0.4 ml.

(4) Integral Elution Amount

In the above described TREF, the integral elution amount determined by integrating the weight proportion of eluted components up to an elution temperature of 10° C. is 10% or less, and that amount determined to an elution temperature of 90° C. is 90% or more, preferably the integral elution amount to an elution temperature of 20° C. is 10% or less and that to an elution temperature of 90° C. is 95% or more, and most preferably the integral elution amount to an elution temperature of 20° C. is 5% or less and that to an elution temperature of 90° C. is 97% or more.

(5) Q Value

The ethylene/α-olefin copolymer of the present invention gives a Q value (weight average molecular weight/number average molecular weight) as determined by size exclusion chromatography (SEC) of 4 or less, preferably 3 or less, more preferably 2.5 or less.

When a resin composition comprising from 50 to 90 wt % of such an ethylene/α-olefin copolymer (a) and from 50 to 10 wt % of high pressure low density polyethylene (b) satisfying the following property requirements (1'), (2'), (3'), and (4') is used as a heat sealable resin, films can be formed in a more stable manner.

(1') MFR

To have an MFR (190° C., 2.16 kg load) as measured in accordance with ASTM D-569 of from 0.1 to 20 g/10 min, preferably from 1 to 13 g/10 min, and more preferably from 2 to 13 g/10 min.

Polyethylenes having an MFR higher than the upper limit result in unstable film formation, while polyethylenes having an MFR lower than the lower limit have poor extrudability and yield a film of poor appearance.

(2') Density

To have a density as measured in accordance with JIS K7112 of from 0.915 to 0.93 g/cm$^3$, preferably from 0.916 to 0.925 g/cm$^3$, and more preferably from 0.918 to 0.922 g/cm$^3$.

Polyethylenes having a density higher than the upper limit have poor low temperature heat sealability, while polyethylenes having a density lower than the lower limit yield films whose surface is too tacky.

(3') Memory Effect (ME)

To have an ME (3 g) of 1.6 or higher, preferably 1.8 or higher, more preferably 2.0 or higher, and most preferably from 2.3 to 5.

Polyethylenes having an ME lower than the lower limit are undesirable in that they provide unstable film formation.

The measurement of ME (3 g) is made with a melt indexer according to JIS K7210 under the conditions of a cylinder temperature of 240° C. and a constant extrusion rate of 3 g/min as follows.

A sample is packed into the apparatus, and only the piston is placed thereon. Six minutes thereafter, the sample begins to be extruded at a predetermined rate. Subsequently, a measuring flask filled with ethyl alcohol is placed directly under the orifice to obtain a straight extrudate.

The diameter (D) of the extrudate is measured with a micrometer. The ME of the sample is determined using the following equation, in which Do is the diameter of the die orifice.

$$ME = D/D_0$$

(4') Melt Tension (MT: melt tension at break)

To have an MT of 1.5 g or higher, preferably 2.5 g or higher, more preferably from 5 g to 15 g. Polyethylenes having too low an MT are undesirable in that the effect of improving processability is reduced.

The high pressure low density polyethylene for use in the present invention has an ME (3 g) and an MT which both satisfy the following relationship.

$$ME \geq [0.05 \times MT + 1.3]/\text{g of polyethylene}$$

This high pressure low density polyethylene has a Q value (weight average molecular weight/number average molecular weight) as determined by size exclusion chromatography (SEC) of from 5 to 30, preferably from 7 to 25, most preferably from 10 to 20.

Although such a high pressure low density polyethylene can be suitably selected from polyethylene products on the market, an especially preferred high pressure low density polyethylene is one produced in an autoclave at a reaction temperature of 220° C. or higher and a reaction pressure of 1,700 kg/cm² or lower.

The ethylene/α-olefin copolymer (a) is blended with the high pressure low density polyethylene (b) in such a ratio that the proportions of ingredient (a) and ingredient (b) are from 50 to 90 wt % and from 10 to 50 wt %, respectively, preferably from 55 to 90 wt % and from 10 to 45 wt %, respectively, and more preferably from 60 to 85 wt % and from 15 to 40 wt %, respectively, an totally 100 wt %.

This heat sealable resin composition comprising ingredients (a) and (b) preferably has an MFR of from 5 to 25 g/10 min, more preferably from 8 to 20 g/10 min, a density of from 0.87 to 0.932 g/cm³, preferably from 0.89 to 0.912 g/cm³, a Q value of from 2 to 10, preferably from 3 to 6, an ME (3 g) of from 1.2 to 2.3, preferably from 1.5 to 2.0, and an MT of 1.0 g to 6 g, preferably 1.5 g or higher, where all test procedures to determine these parameters have been earlier given, with ME and MT satisfying the following relationship.

$$ME \geq (0.2 \times MT + 1)/\text{g}$$

The heat-sealable layer (II) has a lower melting point than the base layer (I). The melting point of the heat-sealable layer (II) is lower by about 8° C. to about 150° C. than that of the base layer (I).

The heat-sealable resin layer (II) in accordance with the present invention has a thickness of from 1 to 10 $\mu$m, preferably from 2 to 8 $\mu$m.

The thickness thereof should be at least 1 $\mu$m in order for the adhesive layer film to melt during blow molding by the thermal action of the parison of molten polyethylene or polypropylene to provide tenacious adhesion between the label and the molding. Thicknesses thereof exceeding 10 $\mu$m are undesirable in that label curling occurs to cause difficulties in offset printing and in label fixing to a mold.

As stated hereinabove, the heat-sealable resin layer of the label is preferably embossed in order to avoid blistering during blow molding, as described in JP-A-2-84319 and JP-A-3-260689.

For example, an embossed pattern having from 5 to 25 lines per 2.54 cm is formed, with the depth of the valleys thereof being from 1 to 8 $\mu$m and being at least ⅓ of the thickness of the heat-sealable resin layer. Embossing is unnecessary for labels for injection molding.

Corona discharge treatment or the like may be conducted, if desired and necessary, to improve the surface printability and adhesion of these in-mold labels.

Printed matter can be formed by gravure printing, offset printing, flexographic printing, screen printing, etc. All such procedures are conventional. The print may contain a bar code, a maker's name, a seller's name, be a character, a trademark, usage, and the like.

A printed and embossed label (1) is cut into a desired shape and size by punching or any other desired procedure. This in-mold label may have such a size as to cover a part of the surface of a container. In general, however, the label is produced as a blank for surrounding the side wall of a container cup, or as a label to be applied to the front and back sides of container bottle produced by blow molding.

Molding

The in-mold label is set in the cavity of the female mold, i.e., the lower mold half, of a differential pressure forming mold in such a manner that the print side of the label is in contact with the cavity wall. The label is then fixed to the inner surface of the mold wall by suction. A sheet or layer of a molten resin which is to form the container is placed over the female mold to conduct differential pressure forming in a conventional way. As a result, a labeled container is molded in which the label has been fused to and united with the external surface of the container wall.

Although the differential pressure forming may be either vacuum forming or air pressure forming, a combination of both is generally preferably carried out with a plug assist. The labels per the present invention are also applicable to blow molding in which a parison of a molten resin is pressed with air pressure against the inner surface of the mold wall.

The labeled container thus produced is free from deformation of the label (1), has excellent adhesion between the container body and the label (1), and has a satisfactory decorative appearance with no blistering, because the label (1) was fixed to the inner surface of the mold before being united with the resin container by integral molding.

The present invention will be explained below in more detail by reference to the following Examples and Comparative Examples.

[I] Methods for Determining and Evaluating Properties

In the Examples and Comparative Examples, properties were determined and evaluated by the following methods.

(1) Determination of Properties (a) MFR: in accordance with ASTM D-569 (190° C., 2.16 kg load).

(b) Density: in accordance with JIS K7112.

(c) ME (memory effect): Measurement was made with a melt indexer according to JIS K7210 under the conditions of a cylinder temperature of 240° C. and a low extrusion rate of 3 g/min in the manner earlier described.

A sample is packed into the apparatus and one piston is placed thereon. Six minutes thereafter, the sample begins to be extruded at a predetermined rate. Subsequently, a measuring flask filled with ethyl alcohol is placed directly under the orifice to obtain a straight extrudate. The diameter (D) of the extrudate is measured with a micrometer. The ME of the sample is determined using the following equation, in which $D_0$ is the diameter of the die orifice.

$$ME = D/D_0$$

(d) Determination of Elution Curve

Using the apparatus shown in FIG. 9, measurement was made in the manner earlier described.

(e) Q Value: Measurement was made by size exclusion chromatography (SEC) under the conditions now given to obtain the weight average molecular weight divided by the number average molecular weight ratio as the Q value. Using a universal calibration curve obtained with monodisperse polystyrene, the molecular weight of each sample was calculated in terms of the molecular weight of linear polyethylene.

(f) MT (melt tension at break): Using Capilograph 1-B, manufactured by Toyo Seiki Seisaku-Sho, Ltd., a sample resin was melted and extruded at a temperature of 190° C. and an extrusion rate of 1 cm/min, while the take-up rate of taking up the extruded molten resin was gradually increased. The stress was measured at the time the resin filament broke. The die used had a length of 8.00 mm, an inner diameter of 2.095 mm, and an outer diameter of 9.50 mm.

(g) Label Punchability

Using a Super Straight Cutter of 20 mm×80 mm, manufactured by K.K. Dumbbell, 50 vertically superposed labels were vertically punched. The resulting cut edges of the labels were visually evaluated for the degree of formation of adherent burrs of the heat sealable resin (protrusions formed by cutting).

○—no burrs.

Δ—slight burrs but no problem in practical use.

×—burrs, a problem in practical use.

(h) Adhesion Strength of Label to Container

A label applied to a container was cut into a width of 15 mm, and the strength of adhesion between the label and the container was determined through tear peeling by means of tensile tester "Autograph Type AGS-D," manufactured by Shimadzu Corp., at a pulling rate of 300 mm/min.

(i) Thermal Shrinkage of Label

Containers were examined for deformation caused by label shrinkage by the following method.

At two days after molding, each of five containers were examined by precisely measuring the girth of an unlabeled part thereof and that of a labeled part thereof with a caliper. Containers in which the difference between the two measured girth values was 1 mm or less are indicated by ○ (good), whereas containers in which that difference was 1 to 2 mm are indicated by Δ, and containers in which that difference was larger than 2 mm are indicated by × (poor).

(j) Coefficient of Friction

In accordance with ASTM D-1894, labels were examined for their coefficient of static friction with respect to the printed side and the heat-sealable layer side using a tensile tester RTM-250, manufactured by Orientec Co., Ltd.

(k) Label Suitability for Insertion into Mold

A hundred labels cut into a size of 60 mm by 110 mm by punching were continuously fed into a mold for blow molding by means of an automatic label feeder manufactured by Pentel Co., Ltd., and the number of label feeding problems (feeding of two labels at a time or a label falling from the mold).

○—no feeding trouble.

Δ—one to five labels suffered a feeding problem.

×—six or more labels suffered a feeding problem.

Ethylene/α-Olefin Copolymer Production Example 1

A catalyst was prepared by the method disclosed in JP-A-61-130314 as follows. To 2.0 mmol of ethylenebis(4, 5,6,7-tetrahydroindenyl)zirconium dichloride complex was added the methylaluminoxane manufactured by Toyo Stauffer Chemical Co., Ltd., in an amount of 1,000 times by mole the amount of the complex. This mixture was diluted with toluene to a total volume of 10 liters to prepare a catalyst solution. Using this catalyst, polymerization was conducted by the following method.

Into an autoclave type continuous reactor having a capacity of 1.5 liters and equipped with a stirrer there was introduced a mixture of ethylene and 1-hexene in such a manner as to result in a 1-hexene proportion of 80 wt %. Polymerization was conducted at 160° C. while maintaining the pressure inside the reactor at 1,600 kg/cm$^2$.

As a result of the polymerization, an ethylene/α-olefin copolymer (1-hexene content, 22 wt %) was obtained which had an MFR of 18 g/10 min, a density of 0.898 g/cm$^3$, a Q value of 1.9 and which gave a TREF elution curve having one peak, with the peak temperature being 50° C. and the value of H/W for that peak temperature being 1.5.

The integral elution amount to 10° C. was 2.1%, that to 20° C. was 3.0%, and that to 80° C. was 100%.

High Pressure Low Density Polyethylene Production Example 2

A high pressure low density polyethylene was produced with an autoclave at a polymerization temperature of 260° C. and a polymerization pressure of 1,500 kg/cm$^2$. The high pressure low density polyethylene thus obtained had an MFR of 4 g/10 min, a density of 0.92 g/cm$^3$, an ME of 2.4, an MT of 10.2 g and a Q value of 10.

Label Production Examples

EXAMPLE 1

(1) A resin composition (A) consisting of 67 parts by weight of polypropylene "Mitsubishi Polypro MA-8" (trade name; melting point, 164° C.), manufactured by Mitsubishi Chemical Corporation, 10 parts by weight of high density polyethylene "Mitsubishi Polyethy EY-40" (trade name; melting point, 132° C.; density, 0.950 g/cm$^3$), manufactured by Mitsubishi Chemical Corporation, and 23 parts by weight of calcium carbonate particles having a particle diameter of 1.5 μm was melt kneaded with an extruder. The melt was extruded at 250° C. through a die into a sheet form, and the sheet was cooled to about 50° C.

Subsequently, this sheet was heated to about 153° C. and stretched 4 times in the machine direction by means of rolls having different peripheral speeds. A uniaxially stretched film was thus obtained.

(2) A resin composition (B) consisting of 51.5 parts by weight of polypropylene "Mitsubishi Polypro MA-3" (trade name; melting point, 165° C.), manufactured by Mitsubishi Chemical Corporation, 3.5 parts by weight of high density polyethylene "EY-40" having a density of 0.950 g/cm$^3$, 42 parts by weight of calcium carbonate particles having a particle diameter of 1.5 μm, and 3 parts by weight of titanium oxide particles having a particle diameter of 0.8 μm was separately melt kneaded at 240° C. with another extruder. This melt was extruded through a die into a film form and laminated to the front side of the film stretched in the machine direction.

On the other hand, a resin composition (C) consisting of 51.5 parts by weight of polypropylene "MA-3 ", 3.5 parts by weight of high density polyethylene "EY-40 ", 42 parts by weight of calcium carbonate particles having a particle diameter of 1.5 μm, and 3 parts by weight of titanium oxide particles having a particle diameter of 0.8 μm and a resin composition (II) for heat sealable resin layer formation consisting of 75 wt % of the ethylene/α-olefin (1-hexene) copolymer obtained in the Production Example 1 given above and 25 wt % of the high pressure low density polyethylene obtained in the Production Example 2 given above were melt kneaded at 200° C. using separate extruders. These melts were fed to a co-extrusion die and laminated to each other within the die, and the resulting laminate film extruded through the die was extrusion-laminated to the back side of the machine-directionally 5-fold stretched sheet of composition (A).

This four-layer film (B/A/C/II) was introduced into a tenter oven, where the film was heated to 155° C. and then stretched 7 times in the transverse direction with a tenter. Subsequently, the stretched film was heated at 164° C. for 1 second for thermal setting, subjected to corona discharge treatment, cooled to 55° C., and then trimmed. Thus, a, microporous stretched resin film having a four-layer structure and a 28% porosity was obtained which had a density of 0.790 g/cm$^3$ and a thickness of 100 μm (B/A/C/II=30/40/25/5 μm).

Layer II had an MFR of 13 g/10 min, a density of 0.904 g/cm$^3$, an ME of 1.7 and an MT of 1.6 g.

Offset printing was conducted on the paper-like layer (B) side of this stretched resin film having the recited laminated four-layer structure. The printed film was passed through embossing rolls to form on the heat-sealable resin layer (II) side an embossed pattern comprising dotted lines at an interval of 1.27 mm (20 lines) and having a valley depth of 8 μm. An enlarged view of this embossed pattern is shown in FIG. 2. The layer (II) had a Bekk's surface smoothness of 480 seconds.

The embossed film was punched to obtain a label (width, 60 mm; length, 110 mm) for blow molding.

This label was fixed by suction to one half of a split-cavity mold for blow molding so that the printed side of the label was in contact with the mold. High density polyethylene "Mitsubishi Polyethy HD BZ-53A" (trade name) having a density of 0.960 g/cm$^3$, a melt index of 0.8 g/10 min, and a melting point of 134° C. was melt-extruded at 230° C. to form a parison, and the mold was then closed. Subsequently, air compressed to 4.2 kg/cm$^2$ was fed into the parison to expand the parison and closely contact the same with the mold. Thus, the parison was formed into a container shape and the label was fused thereto. After cooling, the mold was opened to obtain a labeled hollow container.

This labeled hollow container was free from print fading, and underwent neither label shrinkage nor blistering. The adhesion strength between the container and the label was 750 g/15-mm width.

On the other hand, a propylene homopolymer having an MFR of 1.0 g/10 min was used instead of the high density polyethylene to form a parison. As a result, the adhesion strength between the container and the label was 620 g/15-mm width.

Other properties are shown in Table 1.

EXAMPLE 2

(1) A resin composition (A) was prepared which consisted of 70 wt % propylene homopolymer having a melt flow rate (MFR) of 0.8 g/10 min and a melting point of 164° C., 12 wt % high density polyethylene having a melting point of 134° C., and 18 wt % calcium carbonate having an average particle diameter of 1.5 μm. This composition was kneaded with an extruder set at 270° C., extruded into a sheet form, and cooled with a cooler to obtain an unstretched sheet. This sheet was heated to 145° C. and stretched 5 times in the machine direction to obtain a stretched sheet as layer (A).

(2) A resin composition (C) consisting of 51.5 wt % propylene homopolymer having an MFR of 4 g/10 min and a melting point of 164° C., 3.5 wt % high density polyethylene, and 45 wt % calcium carbonate having a particle diameter of 1.2 μm and a resin composition (B) consisting of 41.5 wt % propylene homopolymer having an MFR of 4.0 g/10 min, 3.5 wt % high density polyethylene, and 55 wt % calcium carbonate having a particle diameter of 1.5 μm were melt kneaded at 250° C. using separate extruders. These melts were fed to a co-extrusion die, laminated to each other within the die, and then co-extruded at 250° C. and laminated to the front side of the film stretched in the machine direction as layer (A) obtained in (1) above.

(3) On the other hand, a resin composition (C) consisting of 51.5 wt % propylene homopolymer having an MFR of 4.0 g/10 min, and a melting point of 164° C., 3.5 wt % high density polyethylene, and 45 wt % calcium carbonate having a particle diameter of 1.2 μm and a heat sealable resin composition (II) consisting of 75 wt % of the ethylene/1-hexene copolymer obtained in one of the Production Examples given above and having an MFR of 18 g/10 min, a density of 0.898 g/cm$^3$, and a Q value of 1.9 and 25 wt % of the high pressure low density polyethylene having an MFR of 4 g/10 min, a density of 0.92 g/cm$^3$, an ME of 2.4, an MT of 10.2. g and a Q value of 10 were melt kneaded at 270° C. using separate extruders. These melts were fed to a die, laminated to each other within the die, and then extruded through the die into a film form and laminated to the back side of the machine-directionally 5-fold stretched sheet as layer (A) so that layer (II) became an outermost layer.

(4) Subsequently, this laminated film was reheated to about 155° C. and then stretched 7 times in the transverse direction. The paper-like layer (layer (B)) of the stretched film was subjected to corona discharge treatment. After being cooled to 55° C., this laminated film was passed through embossing rolls comprising a metal roll and a rubber roll to form on the layer (D) side an embossed gravure pattern comprising dotted lines at an interval of 0.3 mm (80 lines) and having a valley depth of 5 μm.

The embossed film was then trimmed to obtain an in-mold label sheet having a density of 0.91 g/cm$^3$.

The heat sealable resin (II) layer of this label sheet had a Bekk's surface smoothness of 750 seconds.

EXAMPLES 3 TO 5 AND COMPARATIVE EXAMPLES 1 TO 3

In-mold label sheets were obtained in the same manner as in Example 2, except that each of the resin compositions shown in Table 1 was used as the heat-sealable resin composition (II). The label sheets obtained in Examples 3 to 5 and Comparative Examples 1 to 3 were subjected to offset printing, cutting and punching to obtain in-mold labels (1) (width, 60 mm; length, 110 mm). These labels were evaluated for coefficient of friction, suitability for continuous offset printing, and label punchability.

Further, each of these in-mold labels (1) was fixed by suction to one half of a split cavity mold for blow molding so that the printed side of the label was in contact with the mold. High density polyethylene (melting point, 134° C.) was melt-extruded at 200° C. to form a parison, and the mold was then closed. Subsequently, air compressed to 4.2 kg/cm$^2$ was fed into the parison to expand the parison and closely contact the same with the mold. Thus, the parison was formed into a container shape and the in-mold label was fused thereto. After cooling, the mold was opened to obtain a labeled hollow container.

The results of the evaluations of the thus obtained labeled containers for blistering, thermal label shrinkage, and label adhesion strength are shown in Table 1.

Furthermore, labeled hollow containers were obtained in the same manner as above, except that a propylene homopolymer (melting point, 165° C.; MFR, 1.0 g/10 min) was used as a parison material in place of the high-density polyethylene, and melt-extruded at 230° C.

The evaluation results obtained are shown in Table 1.

TABLE 1

|  | Example | | | | Comparative Example | | | Example 5 |
|---|---|---|---|---|---|---|---|---|
|  | 1 | 2 | 3 | 4 | 1 | 2 | 3 |  |
| Composition of heat-sealable resin layer (D) (wt %) | | | | | | | | |
| Ethylene/hexene-1 copolymer obtained in a Production Example | 75 | 75 | 60 | 80 | — | — | — | 100 |
| High pressure low density polyethylene obtained in a Production Example | 25 | 25 | 40 | 19 | — | — | — | — |
| Low density polyethylene, LK-30 | — | — | — | — | 50 | 100 | — | — |
| Ethylene/methyl acrylate copolymer | — | — | — | — | 25 | — | — | — |
| Ziegler-process linear low density polyethylene* | — | — | — | — | 25 | — | — | — |
| Ethylene/vinyl acetate copolymer having a softening point of 108° C. | — | — | — | — | — | — | 95 | — |
| Dibutyl phthalate | — | — | — | 1 | — | — | 5 | — |
| Performance evaluation Adhesion strength (g/15 mm) | | | | | | | | |
| High density polyethylene | 750 | 760 | 750 | 800 | 690 | 650 | 560 | 830 |
| Polypropylene | 620 | 630 | 600 | 650 | 310 | 0 | 220 | 670 |
| Blistering | | | | | | | | |
| High density polyethylene | not occurred | not occurred | not occurred | not occurred | not occurred | not occurred | not occurred | not occurred |
| Polypropylene | not occurred | not occurred | not occurred | not occurred | not occurred | occurred | not occurred | not occurred |
| Degree of burr generation in punching | ○ | ○ | ○ | ○ | ○ | ○ | Δ | ○ |
| Coefficient of static friction | 0.66 | 0.65 | 0.61 | 0.67 | 0.62 | 0.61 | 0.70 | 0.66 |
| Suitability for feeding and taking-off in printing | good | good | good | good | good | good | slight irregularity, but no problem | good |
| Thermal shrinkage of label | ○ | ○ | ○ | ○ | ○ | ○ | ○ | ○ |
| Suitability for insertion of label | ○ | ○ | ○ | ○ | ○ | ○ | ○ | ○ |

*: Linear low-density polyethylene manufactured by Mitsui Petrochemical Industries, Ltd. (ethylene/butene-1 copolymer; density, 0.915 g/cm$^3$)

In-mold labels were obtained which were free from burr generation in punching and showed satisfactory adhesion to polypropylene containers and to high density polyethylene hollow containers.

While the invention has been described in detail and with reference to specific embodiments thereof, it will be apparent to one skilled in the art that various changes and modifications can be made therein without departing from the spirit and scope thereof.

What is claimed is:

1. An in-mold label comprising a thermoplastic resin film base layer (I) carrying printed matter on its front side and, formed on the back side of the thermoplastic resin film base layer (I), a heat sealable resin layer (II) having a lower melting point than the constituent resin of said thermoplastic resin film base layer, the constituent resin of said heat sealable resin layer (II) comprising as the main component an ethylene/α-olefin copolymer obtained by copolymerizing from 40 to 98 wt % ethylene and from 60 to 2 wt % of an α-olefin having from 3 to 30 carbon atoms using a metallocene catalyst.

2. The in-mold label as claimed in claim 1, wherein the ethylene/α-olefin copolymer satisfies the following property requirements (1), (2), and (3):

(1) said copolymer has an MFR of from 2 to 30 g/10 min, (2) said copolymer has a density of 0.935 g/cm$^3$ or less, and (3) upon being subjected to temperature rising elution fractionation (TREF), said copolymer gives an elution curve which has one peak, in which a peak temperature is from 20° to 85° C. and a value of H/W, where H is the height of a peak and W is a peak width at half height, is 1 or larger, and which shows that the copolymer substantially contains one or more components which are eluted at a temperature other than the peak elution temperature.

3. The in-mold label as claimed in claim 1, wherein the heat sealable resin layer (II) consists essentially of a resin composition comprising:

(a) from 50 to 90 wt % ethylene/α-olefin copolymer obtained by the copolymerization of from 40 to 98 wt % ethylene and from 60 to 2 wt % of an α-olefin having from 3 to 30 carbon atoms using a metallocene catalyst, which copolymer satisfies the following property requirements (1), (2), and (3):

(1) the copolymer has an MFR of from 2 to 30 g/10 min, (2) the copolymer has a density of 0.935 g/cm$^3$ or less, and (3) in temperature rising elution fractionation (TREF), said copolymer gives an elution curve which has one peak, in which a peak temperature is from 20° to 85° C. and a value of H/W, where H is the height of the peak and W is a peak width at half height, is 1 or larger, and which shows that the copolymer substantially contains one or more components which are eluted at a temperature other than the peak elution temperature; and (b) from 50 to 10 wt % high pressure low density polyethylene which satisfies the following property requirements (1'), (2'), (3'), and (4'):

(1') the polyethylene has an MFR of from 0.1 to 20 g/10 min, (2') the polyethylene has a density of from 0.915 to 0.93 g/cm$^3$, (3') the polyethylene has a memory effect (ME) of 1.6 or higher, and (4') the polyethylene has a melt tension (MT) of 1.5 g or higher.

4. The in-mold label as claimed in claim 1, wherein the thermoplastic resin film base layer (I) is a microporous laminate resin film comprising a biaxially stretched film base layer (A) comprising from 5 to 30 wt % fine inorganic particles, from 3 to 20 wt % high density polyethylene, and from 92 to 50 wt % polypropylene resin, a paper-like layer (B) laminated to one side of the base layer (A) and consisting of a uniaxially stretched film of a resin composition comprising from 35 to 65 wt % fine inorganic particles, from 0 to 10 wt % high density polyethylene, and from 55 to 35 wt % polypropylene resin, and a paper-like layer (C) laminated to the base layer (A) on a side opposite to the paper-like layer (B) and consisting of a uniaxially stretched film of a resin composition comprising from 35 to 65 wt % fine inorganic particles, from 0 to 10 wt % high density polyethylene, and from 55 to 35 wt % polypropylene resin, the base layer (I) having printed matter on the paper-like layer (B) side and having the heat-sealable resin layer (II) on the paper-like layer (C) side.

* * * * *